(12) United States Patent
Amsden et al.

(10) Patent No.: US 8,529,933 B2
(45) Date of Patent: Sep. 10, 2013

(54) BIPHASIC CALCIUM PHOSPHATE CEMENT FOR DRUG DELIVERY

(75) Inventors: Brian G. Amsden, Kingston (CA); Monica Y. Garcia, Kingston (CA); Ian D. Grant, Belleville (CA); Jeffrey L. Scifert, Arlington, TN (US); Timothy J. N. Smith, Kingston (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 352 days.

(21) Appl. No.: 12/843,357

(22) Filed: Jul. 26, 2010

(65) Prior Publication Data
US 2011/0021427 A1    Jan. 27, 2011

Related U.S. Application Data

(60) Provisional application No. 61/228,641, filed on Jul. 27, 2009.

(51) Int. Cl.
*A61F 2/00* (2006.01)
*A61F 13/00* (2006.01)
*A61F 2/28* (2006.01)

(52) U.S. Cl.
USPC .................. 424/423; 424/422; 623/23.56

(58) Field of Classification Search
None
See application file for complete search history.

(56) References Cited

U.S. PATENT DOCUMENTS

| | | |
|---|---|---|
| 3,899,556 A | 8/1975 | Heide et al. |
| 3,929,971 A | 12/1975 | Roy |
| 4,371,484 A | 2/1983 | Inukai et al. |
| 4,629,464 A | 12/1986 | Takata et al. |
| 4,654,314 A | 3/1987 | Takagi et al. |
| 4,737,411 A | 4/1988 | Graves, Jr. et al. |
| 5,092,888 A | 3/1992 | Iwamoto et al. |
| 5,152,836 A | 10/1992 | Hirano et al. |
| 5,180,426 A | 1/1993 | Sumita |
| 5,281,404 A | 1/1994 | Sumita |
| 5,282,861 A | 2/1994 | Kaplan |
| 5,462,356 A | 10/1995 | Murray |
| 5,747,390 A | 5/1998 | Cooper et al. |
| 5,766,618 A | 6/1998 | Laurencin et al. |
| 5,863,984 A | 1/1999 | Doillon et al. |
| 6,206,957 B1 | 3/2001 | Driessens et al. |
| 6,296,667 B1 | 10/2001 | Johnson et al. |
| 6,323,146 B1 | 11/2001 | Pugh et al. |

(Continued)

FOREIGN PATENT DOCUMENTS

| | | |
|---|---|---|
| EP | 1584338 A2 | 10/2005 |
| WO | 9709286 A1 | 3/1997 |

OTHER PUBLICATIONS

Mastrogiacomo et al. "Reconstruction of Extensive Long Bone Defects in Sheep Using Resorbable Bioceramics Based on Silicon Stabilized Tricalcium Phosphate" Tissue Engineering vol. 12, No. 5, 2006, pp. 1261-1273.*

(Continued)

*Primary Examiner* — Carlos Azpuru
*Assistant Examiner* — Casey Hagopian
(74) *Attorney, Agent, or Firm* — Sorell Lenna & Schmidt LLP

(57) ABSTRACT

This invention relates to biomineral-based cements incorporating biopolymer carriers for the site specific introduction of natural or synthetic compounds that influence bone repair and/or patient recovery. The invention further relates to methods for producing such biphasic calcium phosphate cements for drug delivery.

20 Claims, 7 Drawing Sheets

(56) References Cited

U.S. PATENT DOCUMENTS

| | | | |
|---|---|---|---|
| 6,497,901 | B1 | 12/2002 | Royer |
| 6,949,251 | B2 | 9/2005 | Dalal et al. |
| 2006/0198939 | A1* | 9/2006 | Smith et al. .................... 427/2.1 |
| 2006/0213398 | A1* | 9/2006 | Barralet et al. ............... 106/690 |
| 2006/0240121 | A1* | 10/2006 | Lee et al. ....................... 424/603 |
| 2007/0184035 | A1 | 8/2007 | Pugh et al. |
| 2007/0283849 | A1 | 12/2007 | Edidin et al. |
| 2008/0206296 | A1 | 8/2008 | Bouler et al. |

OTHER PUBLICATIONS

International Search Report and Written Opinion for US Application PCT/US2010/043362 mailed on Nov. 2, 2010.

Camire, St Jean, Machales, Nevsten, Wang, Lidgren, McCarthy, Ginebra: "Material characterization and In vivo behavior of Silicon substituted alpha-Tricalcium phosphate cement" J. Biomedical Mat. Research, vol. 76b, Sep. 23, 2005, pp. 424-431, XP002606102 DOI: 10.1002/jbm.b.30385, the whole document.

Motisuke, Carrodeguas, Zavaglia: "A comparative study between alpha-TCP and Si-alpha-TCP calcium phosphate cement" Key Engineering Materials, vol. 396, Oct. 21, 2008, pp. 201-204, XP002606103, the whole document.

Araujo, Calcium Phosphate Cements Loaded with Pantoprazole as Novel Bone Substitutes, University of Toronto, 2008, pp. 1-98.

Atha et al., Mechanism of Precipitation of Proteins by Polyethylene Glycols, The Journal of Biological Chemistry, vol. 256, No. 23, Issue of Dec. 10, pp. 12108-12117, 1981.

Buxton et al., Bisphosphonate-ciprofloxacin bound to Skelite is a prototype for enhancing experimental local antibiotic delivery to injured bone, British Journal of Surgery Society Ltd, 2004, 91: 1192-1196.

Calafuiori et al., Low Temperature method for the production of calcium phosphate fillers, BioMedical Engineering OnLine, BioMed Central, 2004, pp. 1-10.

Huber et al., First histological observations on the incorporation of a novel nanocrystalline hydroxyapatite paste OSTIM® in human cancellous bone, BMC Musculoskeletal Disorders, BioMed Central, 2006, pp. 1-14.

Komath et al., Development of a fully injectable calcium phosphate cement for orthopedic and dental applications, Bull. Mater. Sci., vol. 26, No. 4, Jun. 2003, pp. 415-422., Indian Academy of Sciences.

Koutsoukos, Current Knowledge of Calcium Phosphate Chemistry and in Particular Solid Surface-Water Interface Interactions, Institute of Chemical Engineering and High Temperature Chemical Processes (FORTH-ICEHT) and Department of Chemical Engineering, University of Patras, Greece, 18 pages.

Barrere et al., Bone regeneration: molecular and cellular interactions with calcium phosphate ceramics, Biomedical Technological Institute (BMTI) University of Twente, Enschede, The Netherlands, International Journal of Nanomedicine 2006: 1 (3) 317-332.

Vila et al., PLA-PEG particles as nasal protein carriers : the influence of the particle size, CAT.INIST, International Journal of Pharmaceutics; ISSN 0378-5173, 2005, vol. 292, 3 pages.

Yuan et al., Preparation of dextran glassy particles through freezing-induced phase separation, ScienceDirect, International Journal of Pharmaceutics: 2007, Abstract, 3 pages.

George, et al., Calcium Phosphate Cement: A New Saviour for Furcation Perforation ?—An in-vitro study, Endodontology, Prof. Dept. of Conservative Dentistry and Endodontic, College of Dental Sciences, Davangere, pp. 7-11.

Lilian Lindsay, M.D.S. Durham, Section of Ondontology,Proceedings of the Royal Society of Medicine, vol. XXXIX, pp. 21-29, Apr. 8, 1946.

Sharma et al., Polyethylene Glycol-Induced Precipitation of Interferon Alpha-2a Followed by Vacuum Drying: Development of a Novel Process for Obtaining a Dry, Stable Powder, AAPS PharmSci 2004, 6 (1) Article 4 (http://www.aapspharmsci.org), Cambridge, MA, pp. 1-14.

Takechi et al., Non-decay type fast-setting calcium phosphate cement using chitosan, Journal of Materials Science: Materials in Medicine 7 (1996) 317-322.

Uchida et al., The Use of Ceramics for Bone Replacement, A Comparative Study of Three Different Porous Ceramics, vol. 6-B, No. 2, Mar. 1984, pp. 269-275.

* cited by examiner

BIPHASIC CALCIUM PHOSPHATE CEMENT FOR DRUG DELIVERY

FIELD OF THE INVENTION

This invention relates to biomineral-based cements incorporating biopolymer carriers for the site specific introduction of natural or synthetic compounds that influence bone repair and/or patient recovery. The invention further relates to methods for producing such biphasic calcium phosphate cements for drug delivery.

BACKGROUND

Orthopedic procedures involving the directed formation of new bone tissue benefit from implantation of biomaterials that stimulate and guide the repair process. The physical properties of the biomaterials in terms of composition and architecture influence the early integration of new bone tissue and ideally enable progressive replacement with natural bone without biological or structural incompatibilities at the implant site. Furthermore, the parallel delivery of therapeutic agents in conjunction with the biomaterials provide for improved clinical outcomes through the acceleration of the bone formation process, the improvement of bone quality, the concomitant reduction of pain, the prophylactic control of infection and other clinical benefits.

Orthopedic surgeons have historically used autograft (bone removed from the patient) as the biomaterial of choice to repair areas of the skeleton damaged by trauma or disease. Discussion on Dental Structure and Dental Caries, *Proc R Soc Med.* 1946 August; 39(10): 637-645. However, high incidences of donor site morbidity, the necessity of a painful second 'harvesting' surgical procedure, and the absence of large quantities of bone available for grafting compromises patient outcomes. Alternate natural sources of bone tissue have also been utilized in the form of allografts (bone taken from a cadaver) and xenografts (bone obtained from animals). However, these are not ideal options due to significant concerns related to: (1) transmission of disease, (2) difficulty of procurement and processing, (3) uncertain immune response, and (4) premature resorption.

In recognition of the limitations of natural bone tissue sources, significant innovation has occurred in the development of synthetic substitutes that attempt to mimic the beneficial features of natural bone while precluding the negative effects. Duplicating the performance advantages of natural bone tissue is challenging as the chemistry, biology and structure of the tissue are all influential in promoting successful orthopedic repair. Uchida, A. et al., The Use of Ceramics for Bone Replacement, *The Journal of Bone and Joint Surgery*, 66-B, 269-275 (1984).

The clinical performance of biomineral-based implants has shown that the chemistry of the implant-bone interface is improved through the use of materials that employ calcium phosphate or similar inorganic compositions. As the main inorganic component of bone consists of a highly substituted calcium phosphate apatite, researchers concerned with developing synthetic bone substitutes have concentrated on the various forms of calcium phosphate. These include hydroxyapatite, carbonated apatite, fluoroapatite, $\alpha$ and $\beta$ tricalcium phosphate, tetracalcium phosphate, octacalcium phosphate, and combinations thereof. In general, these materials have proven to be both biocompatible and osteoconductive and are well tolerated by host tissues. Anna Rita Calafiori et al., Low Temperature Method for the Production of Calcium Phosphate Fillers, *BioMedical Engineering OnLine*, 3:8 (2004); and Franz-Xaver Huber et al., First Histological Observations on the Incorporation of a Novel Nanocrystalline Hydroxyapatite Paste OSTIM® in Human Cancellous Bone, *BMC Musculoskeletal Disorders*, 7:50 (2006).

The important role of biomineral chemistry is highlighted in U.S. Pat. No. 6,323,146 which discloses a synthetic biomaterial compound (Skelite™) composed of silicon-substituted calcium phosphate. Extensive testing demonstrated that this compound is ideally suited for use as a bone substitute material because it is: (1) 100% synthetic, (2) biocompatible, (3) able to participate in the body's natural bone remodeling process, and (4) relatively inexpensive to produce.

A number of other formulations of cements have been developed for orthopedic and/or dental applications. For example, U.S. Pat. No. 5,092,888 provides a hardening material comprising a powder component composed of a mixture of tetracalcium phosphate and calcium phosphate having a Ca/P atomic ratio lower than 1.67 and a liquid component composed of a colloidal aqueous solution comprising solid colloid particles dispersed in an aqueous medium. Also, U.S. Pat. No. 5,180,426 provides a calcium phosphate type setting material comprising a powder composed of at least one of $\alpha$-tricalcium phosphate and tetracalcium phosphate and an aqueous acidic setting solution comprising at least one polysaccharide selected from the group consisting of carboxymethyl chitin, glycol chitin, pullalan, high methoxypectin and chitosan. U.S. Pat. No. 6,949,251 provides a composition comprising porous $\beta$-tricalcium phosphate granules that have a particle size of 0.1-2 mm and that comprise a multiplicity of pores having a pore diameter size of 20-500 µm and being single separate voids partitioned by walls and being not interconnected. U.S. Pat. No. 5,152,836 provides a calcium phosphate cement comprising tertiary phosphate and a calcium secondary phosphate with a molar ratio of Ca/P of 1.400 to 1.498.

The presence of porosity in an orthopedic implant has been recognized as being valuable by many researchers. This has led to a variety of bioceramic implants that can offer porosity of a size that enables new tissue ingrowth, see for example, U.S. Pat. Nos. 3,899,556; 3,929,971; 4,654,314; 4,629,464; 4,737,411; 4,371,484; 5,282,861; 5,766,618; and 5,863,984.

A common technique for producing porous ceramic bodies involves the use of pore forming agents that are removed prior to implantation of the ceramic body; see for example, U.S. Pat. Nos. 4,629,464; 4,654,314; 3,899,556; and International Patent Publication WO 95/32008.

U.S. Pat. No. 4,629,464 discloses a method in which thermally decomposable powdery material (crystalline cellulose) was mixed with hydroxyapatite (HA) powder and drypressed into a desired form. Subsequent thermal processing was used to sinter the HA particles together, providing increased strength, and to create pores in the HA matrix through decomposition of the crystalline cellulose material.

A variation of this technique is disclosed in U.S. Pat. No. 4,654,314 in which bubbled albumen was combined with a calcium phosphate powder and cast into a mold of a desired shape. Subsequent thermal processing hardened, carbonized, and volatilized the albumen pore forming agent, producing a sintered porous calcium phosphate ceramic.

U.S. Pat. No. 3,299,971 discloses a method of producing a porous synthetic material for use in hard tissue replacement. In this method, a porous carbonate skeletal material of marine life (coral) is converted into a porous hydroxyapatite material through a hydrothermal chemical exchange with a phosphate. The final microstructure of the converted hydroxyapatite material is essentially the same as that of the coral from which it was formed. Consequently, pore size is dependent on the type of coral used. While these porous structures possess the appropriate pore size and pore connectivity for hard tissue in-growth, the structure is limited to that of the selected coral and so the production of implants with a solid shell surrounding the porous network (typical of cortical or long bone, for example) is unobtainable. In addition, the bone grafts manufactured using this technique are characterized by poor mechanical properties and are difficult to handle and shape and cannot be secured using standard fixation techniques.

U.S. Patent Publication 2006/0198939 discloses a method of coating a porous calcium phosphate matrix with a polymer to increase the mechanical stability of the matrix and prevent the calcium phosphate matrix from cracking and the pieces from separating.

U.S. Pat. No. 6,485,754 discloses hydroxyapatite based bone cements that contain a cationic antibiotic.

While techniques to form porosity in a bioceramic implant have been established, these techniques are not applicable to a calcium-based cement that has to maintain its moldable property to enable the material to deform and match the contour of the surgical site. Foaming cements have been reported whereby a cement is mixed with a foaming agent that develops bubbles that ultimately generate porosity at the implant site (see US Patent Pub. 2007/0283849). The challenge with this approach is that the implant foaming agent is frequently exhausted prior to implantation, leading to a final product lacking the desired pore size and/or density.

Beyond the formation of a cement-based implant with appropriate chemistry, geometry, structural strength and bone integration, there is the desire to utilize orthopedic implants for the concurrent delivery of therapeutic agents that aid in the repair process.

It is apparent from the aforementioned prior art that a variety of methods have been developed to manufacture bone cements that utilize a biomineral composition. However, current methods and implants possess several shortcomings that make the resultant function of the implant less than satisfactory in terms of new tissue formation, implant stability and long term implant replacement with natural bone. Furthermore, these implants do not provide the capability to effectively deliver therapeutic agents that improve the clinical conditions for the patient.

SUMMARY OF THE INVENTION

The present invention provides a biphasic biomineral and biopolymer based cement that is ideal for local drug delivery of a therapeutic agent at the site of skeletal implantation. In particular, the formulation and application of the product provides the following advantages over the prior art:
a) The chemistry of the biomineral phase of the cement promotes the deposition of new bone tissue and provides a biocompatible interface that precludes implant rejection;
b) The incorporation of a biopolymer phase or network within the cement enables the controlled release of therapeutic agents that influence skeletal repair and the overall recovery of the patient; and
c) The geometry of the biopolymer network and the progressive dissolution of the network following implantation results in the progressive formation of interconnected pathways through the cement to enable new tissue integration.

The invention also provides a calcium phosphate cement, in which at least one dry component, comprising a calcium phosphate based biomineral phase and a biopolymer, and a liquid are combined to form a flowable, paste-like material that is capable of setting into a solid biphasic calcium phosphate cement, which may be used as a structural material in orthopedic, cranio-maxillofacial, dental, and related fields. In addition, the calcium phosphate cement may comprise a therapeutic agent. The calcium phosphate cement of the invention provides a composition where the biopolymer is surrounded by the calcium phosphate forming a substantially biphasic interconnected material. The invention also provides a biphasic interconnected calcium phosphate cement that is not subject to heating once the biphasic composition is produced. In another exemplary embodiment, the invention provides a silicon substituted calcium phosphate based biomineral phase (see U.S. Pat. No. 6,323,146, wherein a portion of the phosphate is substituted with silicon) in combination with a rapidly absorbing biopolymer having an absorption rate in vivo of less than 6 months, less than 4 months, less than 3 months, less than 2 months, less than 1 month, less than 2 weeks, or less than 7 days, a therapeutic agent, and a liquid, wherein the biomineral phase and biopolymer are combined with the liquid (the therapeutic agent may be present in either the liquid or the powder (biomineral and biopolymer phase)) to form a flowable, paste-like material that is capable of setting into a solid biphasic calcium phosphate cement, which may be used as a bone filler or bone growth material in orthopedic, cranio-maxillofacial, dental, and related fields.

In another exemplary embodiment, the invention provides a silicon substituted calcium phosphate based biomineral phase in combination with a rapidly reabsorbing biopolymer having a reabsorption rate in vivo of less than 6 months, less than 4 months, less than 3 months less than 2 months, less than 1 month, less than 2 weeks, or less than 7 days, a therapeutic agent, and a liquid, wherein the biomineral phase and biopolymer are combined with the liquid (the therapeutic agent may be present in either the liquid or the powder (biomineral and biopolymer phase)) to form a flowable, paste-like material that is capable of setting into a solid biphasic calcium phosphate cement, which may be used as a structural material in orthopedic, cranio-maxillofacial, dental, and related fields.

The invention also provides a silicon-stabilized calcium phosphate cement kit, comprising a powder having silicon-stabilized calcium phosphate particles and a rapidly reabsorbing biopolymer having a reabsorption rate in vivo of less than 6 months, less than 4 months, less than 3 months, less than 2 months, less than 1 month, less than 2 weeks, or less than 7 days, in a first container, a second container containing a lyophilized protein and a third container containing a liquid, wherein the liquid is combined with the lyophilized protein to dissolve the protein in the liquid and the combined protein/liquid is then combined with the powder to form a flowable, paste-like material that sets into an essentially biphasic cement comprising a silicon-stabilized calcium phosphate biopolymer mixture.

The biphasic calcium phosphate cement may be used as a bone growth inducing material in orthopedic, cranio-maxillofacial, dental, and related fields. In addition, the silicon-stabilized calcium phosphate cement may comprise a therapeutic agent in association with the biopolymer and/or the biomineral phase. In an exemplary embodiment, a calcium phosphate precipitate is produced and doped with a desired amount of silicon and spray-dried to remove moisture and produce a desired particle size, which particles may be milled or sieved to control the particle size, the resulting calcium phosphate particles are then sintered to produce the silicon-stabilized calcium phosphate particles of the biomineral phase, which may be further milled and/or sieved. The silicon-stabilized calcium phosphate particles comprises between about 0.5% and about 5% silicon by weight, between about 1% and about 2.5% silicon by weight or between about 1% and about 2% silicon by weight, where the calcium phosphate and silica may be sintered at a temperature of between about 900° C. to about 1,500° C., between about 1,000° C. to about 1,400° C., between about 1,000° C. to about 1,300° C., between about 1,100° C. to about 1,300° C., between about 1,100° C. to about 1,200° C., and/or at about 1175° C. In another exemplary embodiment, the calcium phosphate phase comprises particulate material that has been sieved into a size range of about 50 to about 350 μm.

The silicon-stabilized calcium phosphate of the biomineral phase may comprise α-tricalcium phosphate (α-TCP) at an amount of between about 50% to about 100%, between about 70% and about 90% or about 75% to about 85% of the calcium phosphate present in the biphasic cement. The remaining calcium phosphate may be substantially in the form of hydroxyapatite, however other forms may be present as well.

The biopolymer may be present at a concentration between about 5% to about 75%, between about 10% to about 50%, between about 15% to about 30%, by weight.

The present invention also relates to a settable biomineral composition comprising a plurality of individual calcium phosphate particles, a liquid capable of supporting calcium phosphate precipitation, and a bioabsorbable polymer present at a concentration wherein the bioabsorbable polymer forms fluidly connected network around which the calcium phosphate particles are deposited during setting of the final composition. In another exemplary embodiment, the settable biomineral composition comprises silicon-substituted calcium phosphate particles. In another exemplary embodiment, the calcium phosphate particles are at least 50% tricalcium phosphate. In yet another exemplary embodiment, the biopolymer contains one or more therapeutic agents, such as growth factors, analgesics and/or an antimicrobial agent.

The present invention also relates to a settable biomineral composition that retains a dough like consistency for a time sufficient to allow a physician or medical professional to mold the composition into a desired shape, wherein the composition subsequently hardens to form a biphasic implant comprising calcium phosphate phase and a bioabsorbable polymer phase, wherein each phase forms a separate but intertwined lattice structure. In another exemplary embodiment, the composition comprises silicon-substituted calcium phosphate particles. In another exemplary embodiment, the biphasic composition sets within about 60 minutes, within about 30 minutes, within about 20 minutes, within about 15 minutes, within about 10 minutes, within about 5 minutes, or within about 3 minutes. In yet another exemplary embodiment, the biopolymer contains one or more therapeutic agents, such as growth factors, analgesics and/or an antimicrobial agent.

The invention also relates to a kit having a dry component comprising silicon-substituted calcium phosphate particles, a liquid component, and a bioabsorbable polymer at a concentration wherein the bioabsorbable polymer forms a fluidly connected network around which the calcium phosphate particles are bonded after mixing the dry component and the liquid component to produce a cement.

In another exemplary embodiment, the invention provides a method for the production of a biphasic calcium phosphate cement, comprising mixing a silicon-substituted calcium phosphate powder, a biopolymer and an aqueous solution, and producing an in vivo settable biphasic calcium phosphate cement. In another exemplary embodiment, the invention relates to silicon-substituted calcium phosphate particulates having up to about 5 weight percent silicon substituted into the compound. In another exemplary embodiment, the biopolymer network is present at less than about 35, or less than about 25, weight percent of the silicon-substituted calcium phosphate particulates. In another exemplary embodiment, the biopolymer network is present in an amount greater than 2% and less than 35% weight percent of the silicon-substituted calcium phosphate particulates.

In another exemplary embodiment, the biopolymer does not improve the stability of the biomineral phase, the biomineral phase is not more than about 35% or 25% hydroxyapatite in the final product, the biopolymer network in the final product does not dissolve rapidly in a aqueous environment, the final calcium phosphate particles of the biomineral phase have been sintered prior to incorporation into a kit or composition of the invention, the composition or powder phase excludes the addition of dicalcium phosphate and/or calcium carbonate and/or excludes an effective amount of an effervescent agent.

In an exemplary embodiment, the biopolymer network may comprise a therapeutic agent, for example, the biopolymer network may comprise polyethylene glycol or a polysaccharide, e.g., dextran, alginate and/or chitosan, based polymer in combination with one or more therapeutic agents, including, but not limited to, members of the BMP protein family, such as osteogenically active forms of OP-1, OP-2, OP-3, BMP-2, BMP-3, BMP-4, BMP-5, BMP-6, BMP-9, BMP-10, BMP-11, BMP-13, BMP-15, GDF-1, GDF-3, GDF-5, GDF-6, GDF-7, and amino acid sequence variants thereof. See U.S. Patent Pubs. 2008/0014250 and 2009/0048412. Particularly advantageous therapeutic agents include a morphogenetic protein that is capable of inducing a progenitor cell to form cartilage and/or bone, analgesics and/or antibiotics.

In another exemplary embodiment, the therapeutic agent is not lyophilized onto the silicon-stabilized calcium phosphate cement. In yet another exemplary embodiment, the biopolymer comprises two or more molecularly dissimilar polymers, for example, one polymer may provide mechanical strength and a second polymer may impart desirable release properties for a therapeutic agent. In another example, one polymer may be high soluble to enable rapid formation of voids in the cement, which encourage bone integration.

In an exemplary embodiment, the invention comprises a kit having a lyophilized protein, such as BMP-2, in a first container, a second container having an aqueous liquid, such as a sodium phosphate based buffer, and a third container having a powder comprising silicon-stabilized calcium phosphate. The biopolymer may be present in either the second container or the third container, however if the biopolymer is present in the aqueous liquid container the biopolymer must be non-soluble in such aqueous liquid. Optionally, the third container may also contain calcium chloride. A biphasic calcium phosphate cement containing the lyophilized protein may be made by rehydrating the protein in the aqueous liquid from the second container and then mixing the aqueous liquid protein mixture with the powder contained in the third container to form a bone cement.

In an exemplary embodiment, the invention comprises a kit having a lyophilized protein, such as BMP-2, in a first container, a second container having an aqueous liquid, and a third container having a powder comprising silicon-stabilized calcium phosphate, PEG and sodium phosphate. Optionally, the kit may also contain a calcium salt. A biphasic calcium phosphate cement containing the lyophilized protein may be made by rehydrating the protein in the aqueous liquid from the second container and then mixing the aqueous liquid protein mixture with the powder contained in the third container to form a bone cement. For example, upon reconstitution, each milliliter of a rhBMP-2 solution contains:
1.5 mg of rhBMP-2;
5.0 mg sucrose;
25 mg glycine;
3.7 mg L-glutamic acid;
0.1 mg sodium chloride;
0.1 mg polysorbate 80; and
1.0 mL of sterile water.
Which may be mixed with a powder comprising about 1 gram of PEG and 4 grams of silicon-stabilized calcium phosphate particles, which may optionally contain sodium phosphate as well.

In another exemplary embodiment, the invention comprises a kit having a first container of an aqueous liquid such as a sodium or potassium phosphate based buffer, and a second container having a powder comprising silicon-stabilized calcium phosphate, a therapeutic agent, such as BMP-2, and a biopolymer. A biphasic calcium phosphate cement may be made by mixing the liquid and powder components of the kit to produce a composition having a moldable dough like consistency. In another exemplary embodiment, the invention comprises a kit having a first container of an aqueous liquid comprising a sodium or potassium phosphate based buffer and an amino acid modified dextran, and a second container having a powder comprising silicon-stabilized calcium phosphate and a calcium salt, such as calcium chloride, optionally the powder may also comprise a lyophilized protein, such as BMP-2, and/or a biopolymer. In yet another exemplary embodiment, the invention comprises a kit having a first container of an aqueous liquid comprising a sodium or potassium phosphate based buffer and an amino acid modified dextran, and a second container containing calcium phosphate, for example, tricalcium phosphate and/or silicon-stabilized calcium phosphate. Either the powder and/or the liquid may also comprise a therapeutic agent, such as BMP-2, and/or the biopolymer. In these exemplary embodiments, when the biopolymer is not present in the powder, it is present in the aqueous liquid.

In another exemplary embodiment, the invention comprises a kit having a container of an aqueous liquid such as a sodium phosphate based buffer, and a container having a powder comprising silicon-stabilized calcium phosphate and a biopolymer containing a therapeutic agent incorporated therein. For example, the biopolymer may be a stable colloidal suspension comprising small particles comprising a linear, peptide-linked, polyamino acids having hydrophilic amino acids and hydrophobic repeating acid and a therapeutic agent in association therewith. A bone cement may be made by mixing the aqueous liquid, biopolymer and powder to form the bone cement.

In another exemplary embodiment, the invention comprises a kit having a first container of an aqueous liquid such as a sodium phosphate based buffer, and a second container having a powder comprising silicon-stabilized calcium phosphate and a biopolymer containing a therapeutic agent associated therewith. For example, the biopolymer may be a solid support material consisting of at least one cross-linked insolubilized dextran derivative and a therapeutic agent in association therewith. A bone cement may be made by mixing the contents of the first container with the contents of the second container to form the bone cement.

The biopolymer of the invention preferably is absorbed in vivo rapidly, thereby releasing greater than 40%, greater than 50%, greater than 60%, greater than 70%, or greater than 80% of the entrapped therapeutic agent over a period of about 30 days.

The invention also provides a kit comprising a first container comprising a dry component, such as a calcium phosphate based biomineral phase and a biopolymer, and a second container comprising a liquid component, wherein the dry component and liquid component may be mixed together to form a flowable, paste-like material that then sets into a solid calcium phosphate cement. Optionally, a setting accelerant, such as sodium or potassium phosphate, with or without an additional calcium salt such as calcium chloride, may be added to the powder and/or the liquid, and likewise a therapeutic agent may be added to the powder and/or liquid.

DETAILED DESCRIPTION OF THE INVENTION

Figure 1:
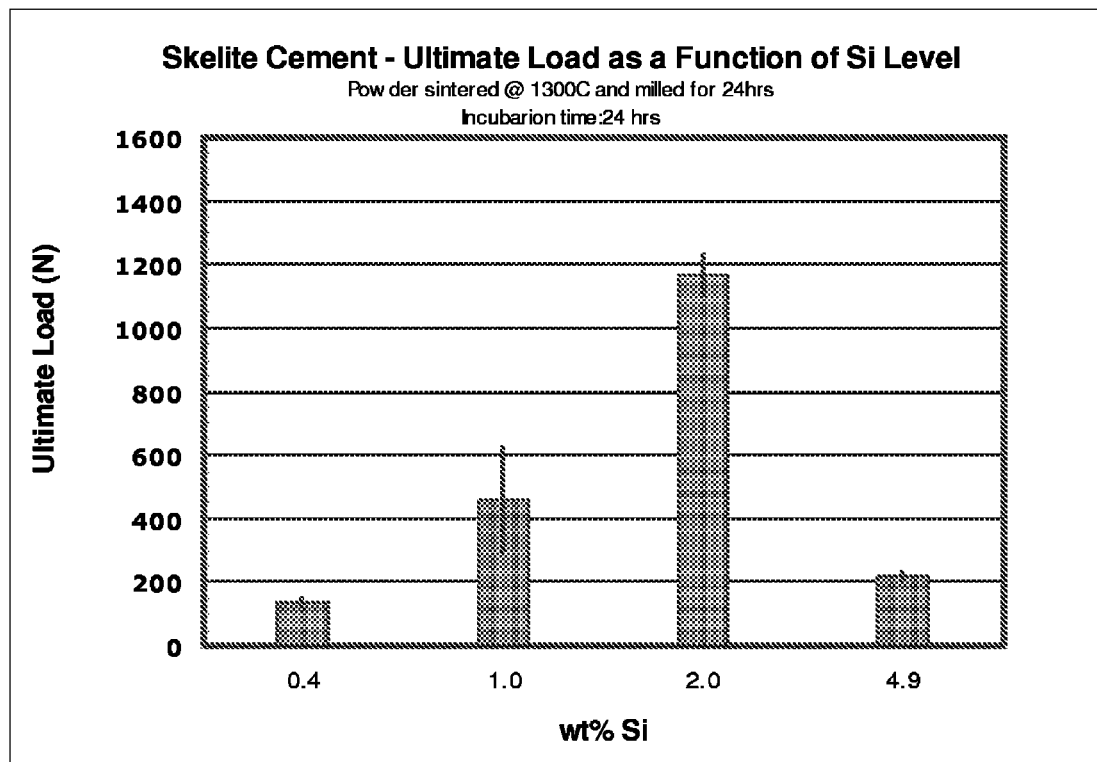
FIG. 1 illustrates the ultimate load of an exemplary composition as a function of wt % silicon addition during the cement precursor manufacturing process when utilizing a 1300 C sintering step.

For the purposes of the instant disclosure, the following definitions are provided.

As used herein, "biomineral phase" means a composition comprising calcium phosphate, which may or may not be substituted or augmented with additional elements, such as silicon, magnesium, and/or aluminum.

As used herein, "biopolymer" means a biocompatible molecule or mixture of molecules that is/are dissolved and/or degraded in the body, examples include polyethylene glycol, dextran and any modifications thereof that are well tolerated by the human body. A biopolymer as used herein does not need to be a polymer produced by a living organism, although it may be.

As used herein, "biopolymer network" means biopolymer particles substantially surrounded by the biomineral phase and in fluid communication with one or more adjacent biopolymer particles or clusters of biopolymer particles, but does not require direct biopolymer particle to particle contact throughout the composition.

As used herein, "biphasic calcium phosphate cement," "biphasic biomineral-based cement" and similar phrases mean a settable composition comprising at least two distinct and intermixed phases, a biomineral phase and a biopolymer phase, however the phrase is not intended to limit the composition to solely two phases as will be evident from the fact that the therapeutic agent may be considered a third phase in some embodiments.

As used herein, "calcium phosphate powder," "powder" or derivatives thereof means a solid substance comprising calcium phosphate in the form of small loose particles and other compounds in a dry or substantially dry state.

As used herein, "setting time" and other such phrases means the cement has substantially hardened, but is not yet not completely rigid, for example, having a ranking of 4 as described herein.

As used herein, "therapeutic agent" means an agent that promotes, induces, increases, or accelerates bone growth or healing, decreases or prevents growth of undesirable bacteria or fungi, reduces or eliminates the sensation of pain in the patient and/or other agents that provide a beneficial effect to a patient or subject. Suitable therapeutic agents include, but are not limited to, antibiotics such as tetracyclines (e.g., minocycline), rifamycins (e.g., rifampin), macrolides (e.g., erythromycin), penicillins (e.g., nafcillin), cephalosporins (e.g., cefazolin), other beta-lactam antibiotics (e.g., imipenem, aztreonam), aminoglycosides (e.g., gentamicin), chloramphenicol, sulfonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole) and beta-lactam inhibitors (e.g., sulbactam); analgesics such as acetaminophen, aspirin, clonidine, flurbiprofen, indoprofen, naproxol, pentazocine, proxazole, tramadol, verilopam, volazocine, xylazine, zucapsaicin, phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, morphine, heroin, hydromorphone, metopon, oxymorphone, levorphanol, codeine, hydrocodone, oxycodone, nalorphine, naloxone, naltrexone, salycilates, phenylbutazone, indomethacin, and phenacetin; anticytokines; cytokines; anti-interleukin-1 components (anti-IL-1); anti-TNF alpha; stem cells, including autogenic or allogenic mesenchymal stem cells, bone marrow aspirate, and/or adipose tissue-derived stromal cells; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Fibroblast Growth Factors (FGFs); Platelet Derived Growth Factors (PDGFs), including PDGF-A, PDGF-B, PDGF-C, and PDGF-D; Growth Differentiation Factors, including rhGDF-5; insulin-related growth factor-I (IGF-I); insulin-related growth factor-II (IGF-II); fibroblast growth factor (FGF); beta-2-microglobulin (BDGF II); Bone Morphogenetic Proteins (BMPs), including BMP-2, BMP-7 and BMP-12; Transforming Growth Factor betas (TGF-βs), including TGF-β-1, TGF-β-2, and TGF-β-3; Nell-1 protein; LIM mineralization protein and peptides (see U.S. Patent Publication 2005/0196387); matrix metalloproteinases (MMP) inhibitors; and combinations thereof. For example, the biopolymer and/or biphasic calcium phosphate cement may contain gentamicin and rhBMP-2.

The term "therapeutically effective amount" means a quantity of a therapeutic agent which, when administered to a patient or subject, is sufficient to result in an improvement in the subject's condition. The improvement may be determined in a variety of ways. Additionally, the improvement does not mean a cure and may include only a marginal change in the subject's condition.

The invention is directed to a biphasic calcium phosphate cement comprising a biopolymer network within a biomineral phase that enables the progressive release of therapeutic agents to facilitate local bone repair and/or systemic treatments.

The role of the biopolymer network is three-fold:
a) The biopolymer improves the handling properties of the implant upon initial formation of the biphasic calcium phosphate cement;
b) The biopolymer is soluble and/or degradable under the conditions present at a skeletal implant site and, as a result, the progressive dissolution/degradation of the biopolymer releases the therapeutic agent or combination of therapeutics agents that are either incorporated into the biopolymer or present as a tertiary phase that is primarily accessible upon removal of the biopolymer;
c) The progressive removal of the biopolymer by dissolution/degradation generates an expanding network of interconnected pores through the calcium phosphate phase which are subsequently filled with natural bone tissue, thereby stabilizing and integrating the implant into the area of skeletal repair.

In the preparation of a biphasic calcium phosphate cement according to the invention, importance is attached to the handling of the product at the time of surgical implantation. Biphasic calcium phosphate cements are ideally malleable to enable the material to be formed and molded in the operating room to match the contours of the damaged bone. Once inserted and crafted to the desired final shape, the cement needs to maintain position and shape through the stiffening and strengthening of the mechanical properties, which is typically described as setting. The formulations of the invention may be mixed as a two part composition involving a reactive calcium phosphate phase and a liquid phase that allows the composition to set. The composition may comprise additional setting agents that function as accelerants or inhibitors of the setting reaction based on their specific influence on the short term crystallization effects (i.e., setting) following hydration of the powder. Exemplary agents are described in the literature, for example Driessens et al. (1993), *J Mater Sci Mater Med* 4:503. The two part composition is stable during storage in the form of isolated components and only undergoes a setting reaction when mixed, which is typically at the time of surgery.

The incorporation of a biopolymer network into the biomineral phase can be achieved by the addition of biopolymer particles of known geometrical properties and volume ratio relative to the biomineral phase. Particle packing theory supports the identification of volume ratios for a two phase mixture whereby the particles of the aggregate phase become connected and form a continuous network throughout the second distributed phase. Accordingly, the addition of biopolymer particles to a two part cement composition, at a volume ratio above an established threshold, results in a network of biopolymer particles dispersed throughout the cement.

Selection of the biopolymer influences the properties of the three part mixture (i.e. biomineral phase, setting agent and biopolymer network) with respect to mixing characteristics, handling at the time of surgical placement, mechanical performance following setting, and therapeutic agent release profiles. An ideal biopolymer enables easy incorporation of the biopolymer into the biomineral phase followed by progressive release of an incorporated therapeutic agent according to a desired profile. One such candidate for the biopolymer is polyethylene glycol (PEG), another biopolymer is a modified dextran such as those disclosed in U.S. Pat. Nos. 6,946,443, 7,101,863, and 6,946,443, another biopolymer comprises a carboxymethyl dextran modified by Tryptophan, Phenylalanine, or Tyrosine, see U.S. Patent publication 2009/0048412. Alternate preferred polymers are alginate, collagen, gelatin and polycaprolactone. Preferred biopolymer features are relatively high solubility to enable pore formation early in the bone integration process, freedom from toxic breakdown products, an ability to support the addition of therapeutic agents, and properties that encourage a setting time of 15 to 60 minutes.

Additional biopolymers that may be used in the invention include, but are not limited to, lactose based particles, hyaluronate, modified dextrans, poly(acrylic acid), poly(cyanoacrylates), poly(amino acids), poly(anhydrides), poly (depsipeptide), poly(esters) such as poly(lactic acid) or PLA, poly(lactic-co-glycolic acid) or PLGA, poly(hydroxybutyrate), (dioxanone); poly(ethylene glycol), poly(hydroxypropyl) methacrylamide, poly(organo) phosphazene, poly(ortho esters), poly(vinyl alcohol), poly(vinylpyrrolidone), maleic anhydride-alkyl vinyl ether copolymers, pluronic polyols, albumin, cellulose and cellulose derivatives, fibrin, oligosaccarides, glycaminoglycans, sulfated polysaccharides, PLA-PEG particles, blends and copolymers thereof. Because the biopolymers of the invention weaken the physical strength of the silicon substituted calcium phosphate matrix, it is beneficial to maintain the biopolymer at a concentration of 30% wt. or less relative to the silicon substituted calcium phosphate matrix. In an exemplary embodiment, the biopolymer is processed so as to produce pores in the cement that are between about 100 µm to about 400 µm, about 100 µm to about 300 µm, about 100 µm to about 200 µm. For example, dried PEG may be milled, ground and/or sieved to obtain an average particle size of about 200 µm.

Use of PEG and/or dextran as the biopolymer has several advantages. For example, where the therapeutic agent is a protein the protein may be recovered from a solution by PEG and/or dextran precipitation, which may optionally contain additional mannitol and/or trehalose to stabilize the protein, and the precipitate, which may optionally be further dried, may then be used either alone or be combined with additional biopolymer in the formulation of the biphasic calcium phosphate cement. D. H. Atha and K. C. Ingham (1981), Mechanism of Precipitation of Proteins by Polyethylene Glycol, *J. Biol. Chem.* 256(23):12108-12117 and Sharma V K, Kalonia D S. (2004), Polyethylene Glycol-Induced Precipitation of Interferon Alpha-2a Followed By Vacuum Drying: Development of a Novel Process for Obtaining a Dry, Stable Powder, *AAPS PharmSci.* 6 (1): article 4. DOI: 10.1208/ps060104. Alternatively, a therapeutic agent/biopolymer combination may be created by lyophilization of a therapeutic agent-PEG aqueous mixture, for example, a rhBMP-2-PEG mixture may be lyophilized and the resulting material may be formed into particles of the appropriate size. International Publication WO/2003/000014.

A co-solution of dextran and PEG may be gradually frozen to produce dextran particles after lyophilizing the frozen solution and re-dissolving the continuous phase (PEG) in dichloromethane or acetonitrile. This process may be used to create particles ranging in diameter between 200 nm and 10 µm by selecting the molecular weights of PEG and dextran, concentration of the co-solution, and PEG/dextran ratio. For example, a biopolymer such as an amino acid modified dextran (see U.S. Patent Pub. 2009/048412) may also include a therapeutic agent encapsulated therein or associated therewith. W. Yuana, F. Wua, Y. Genga, S. Xua and T. Jin (2007), Preparation of dextran glassy particles through freezing-induced phase separation, *Intern. J. Pharm.* 339(1-2):76-83, doi:10.1016/j.ijpharm.2007.02.018.

The incorporation of a biopolymer network within the biomineral phase affords great flexibility in the delivery of therapeutic agents. One or more therapeutic agents may be incorporated into the precursor biopolymer particles at the time of preparation of the precursor particles. Based on the properties of the biopolymer and the therapeutic agent, the opportunity exists for an extended shelf life of the particles containing the therapeutic. For example, an aqueous solution of a therapeutic agent such as a protein (e.g., BMP-2, BMP-12, Op-1, and/or GDF-5) may be precipitated using PEG and the resulting precipitate dried and optionally milled to a desirable size, to form a biopolymer network incorporating the therapeutic agent.

It is also possible to form the biopolymer particles as hollow shells that contain an inner volume that can be occupied by the therapeutic agents. This approach may allow rapid release, as the relative volume of biopolymer to the therapeutic agent may be low and consequently the dissolution/degradation rate of the biopolymer may allow relatively quick release of the therapeutic agent within the biphasic calcium phosphate cement.

The selection of the therapeutic agents may be based on singular or combinations of therapies. Furthermore, the configuration of the network may be adjusted to accentuate or retard the release rate of the agent.

The use of rhBMP-2 as an accelerator of bone repair has been well documented in scientific and clinical research. The delivery of such an agent can be achieved through the use of the biopolymer network and biomineral phase. Furthermore, the release rate and duration can be adjusted based on the properties of the biopolymer network.

Orthopedic surgery commonly results in post-operative pain. The incorporation of pain management agents may result in local pain site relief and greater flexibility in overall pain management via secondary systemic pain management tactics.

Noting that orthopedic surgery is invasive and accordingly there is the risk of microbial infection, an antimicrobial drug may be introduced as the therapeutic agent. Thus, the therapeutic agents of the invention include bone morphogenetic proteins, analgesics, anti-microbials and other such agents.

A combination of therapeutic agents is also possible where compatible drugs are mixed together as part of the preparatory process and then delivered simultaneously following implantation.

A combination of therapeutic agents can also be delivered whereby one agent is integrated within the material forming the biopolymer network and a second agent is entrapped between the biopolymer and the biomineral phases.

Multiple options are available for the site specific delivery of the biomineral phase in combination with the biopolymer network. For cements that are easily formable prior to setting, the composition may be delivered by injection, cannula or catheter. For cements that exhibit high viscosity, application to the implant site may be by direct surgical access or by the pre-formation of pellets that are subsequently placed in proximity to the area of skeletal damage. Setting times may be measured according to the international standard ISO 1566 for dental zinc phosphate cements.

In an exemplary embodiment the invention provides a silicon-substituted calcium phosphate powder and an aqueous liquid along with a biopolymer. While the biopolymer may be present in either the powder or the liquid components, it may be desirable to have the biopolymer present in the powder component prior to mixing. The physical state of the powder, such as the size distribution of the particles, may be modified to affect the reactivity, since the main reaction in setting of the cement is hydration by water, which is influenced by the surface area of the silicon-substituted calcium phosphate particles in the powder. In an exemplary embodiment the silicon-substituted calcium phosphate particles have a size distribution around 3 μm to 7 μm and the biopolymer has a size distribution around 200 μm, wherein the biopolymer is inert during the setting of the cement around the biopolymer beads, granules, flakes or strands and the liquid component comprises an accelerant, such as $Na_2HPO_4$, $NaH_2PO_4$, $KH_2PO_4$, $K_2HPO_4$, or mixtures thereof, in a concentration of 0.5-5% (wt/vol.), based on the liquid phase.

Additional options exist for the use of biopolymers that can be modified in terms of polymeric crosslinking at the time of application.

In summary, the present invention provides a biomineral phase in combination with a biopolymer network that has numerous advantages over the prior art and beneficial uses in the field of orthopedics and dentistry. The biphasic calcium phosphate cement provides a scaffolding for an orthopedic implant that may be formed to the exact shape required to repair a skeletal defect. Furthermore, the cement contains both calcium and phosphorous elements that encourage new bone deposition. In addition, the biphasic calcium phosphate cement may be produced with a composition that actively stimulates remodeling of the implant and the progressive replacement by natural bone tissue. The biopolymer network of the composition provides for the progressive formation of passageways through the cement by virtue of the dissolution/degradation of the biopolymer. The formation of such passageways enables progressive bone tissue integration throughout the cement and results in enhanced bone regeneration and healing. The biopolymer may additionally incorporate one or more therapeutic agents that are released in a controlled manner as part of the dissolution/degradation of the biopolymer.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of chemistry and general processing methods for the ceramics referred to but not explicitly described in this disclosure and examples are reported in the scientific literature and are well known to those skilled in the art.

EXAMPLES

Example 1

Preparation of a Biphasic Calcium Phosphate Cement

A biphasic calcium phosphate cement precursor was initiated through a wet chemistry process. An ammoniated ammonium phosphate solution was added drop wise to an aqueous solution of calcium nitrate to form a calcium phosphate (Ca—P) precipitate which was subsequently aged for 22 hours under conditions of agitation to ensure the reaction had progressed to completion. In order to enhance the biological activity of the final biomineral composition, silicon was added as a finely dispersed fumed silica. The silica doped Ca—P precipitate was subsequently centrifuged, decanted and spray dried. The resulting silicon-stabilized calcium phosphate powder (U.S. Pat. No. 6,323,146) was calcined in alumina crucibles to remove water and residual precursor reactants.

In order to form a cement, the above biomineral was mixed with a buffer solution ($Na_2HPO_4$). In addition to the inclusion of the buffer solution, a soluble biopolymer was added in the form of polyethylene glycol (PEG). The ratio of the components influences the following properties:
a) viscosity of the mixture prior to setting (from injectable to putty)
b) internal porosity following dissolution of the soluble biopolymer phase
c) Mechanical properties of the cement following the setting process
d) Total drug delivery capacity Example 2

Optimizing the Mechanical Performance of the Biphasic Calcium Phosphate Cement

An evaluation of the critical parameters influencing the properties of the cement was undertaken as a means to select the cement formulation that maximizes performance. A series of cements were prepared according to the procedure outlined in Example 1; however, certain parameters were adjusted in the pursuit of optimized performance.

Figure 2:
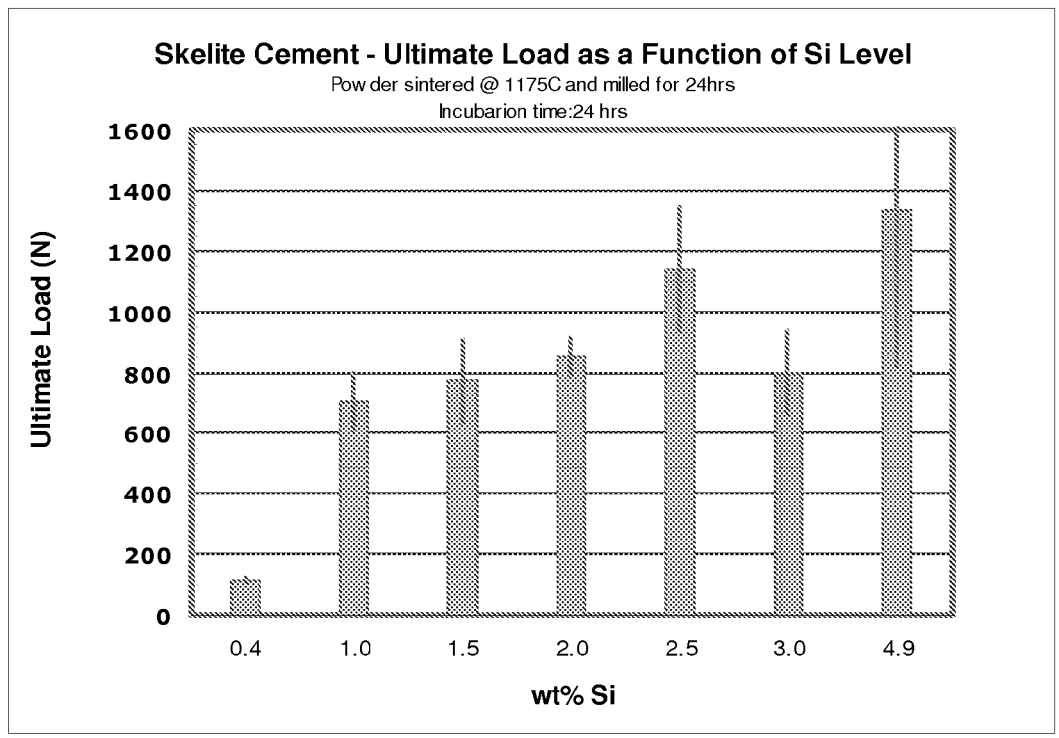
FIG. 2 illustrates the ultimate load as a function of wt % silicon addition during the cement precursor manufacturing process when utilizing a 1175 C sintering step.

As evidenced in FIGS. 1 and 2, the ultimate load of the biphasic calcium phosphate cement (following the setting process) is dependent upon the wt % of silicon added during the manufacturing of the biomineral precursor.

Figure 3:
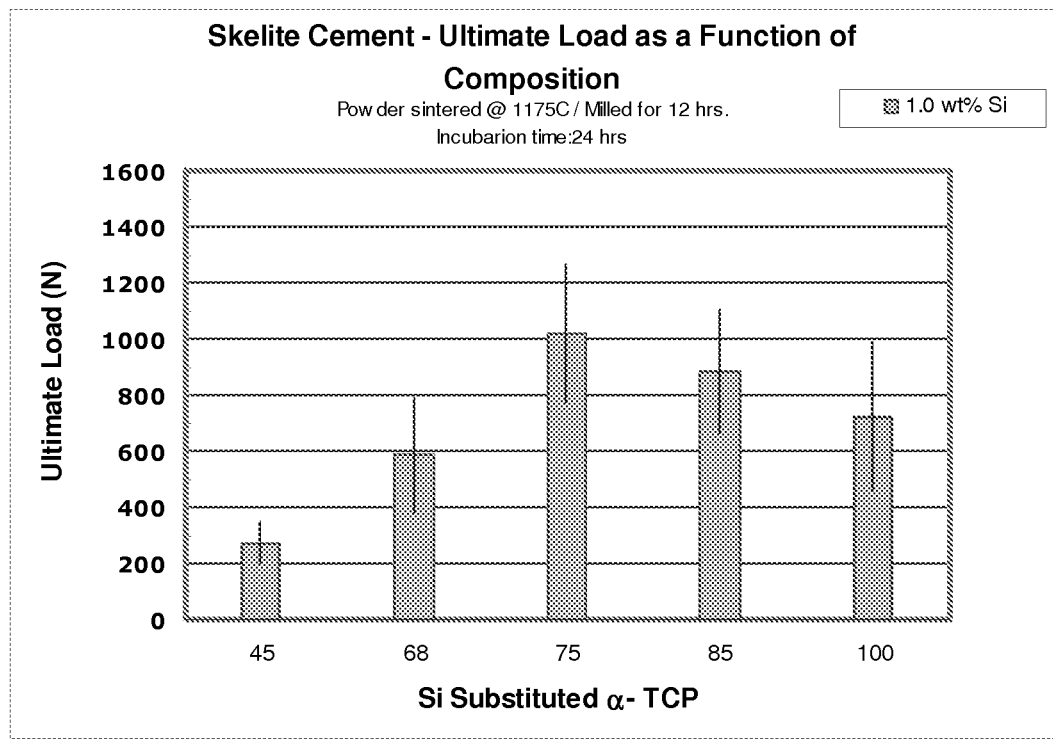
FIG. 3 illustrates the ultimate load as a function of $\alpha$-TCP % in the cement precursor when utilizing 1.0 wt % silicon and a 1175 C sintering step.

FIG. 3 indicates that the ultimate load of the biphasic calcium phosphate cement is influenced by the phase mixture of the precursor Ca—P powder used for production of the biomineral phase.

Figure 4:
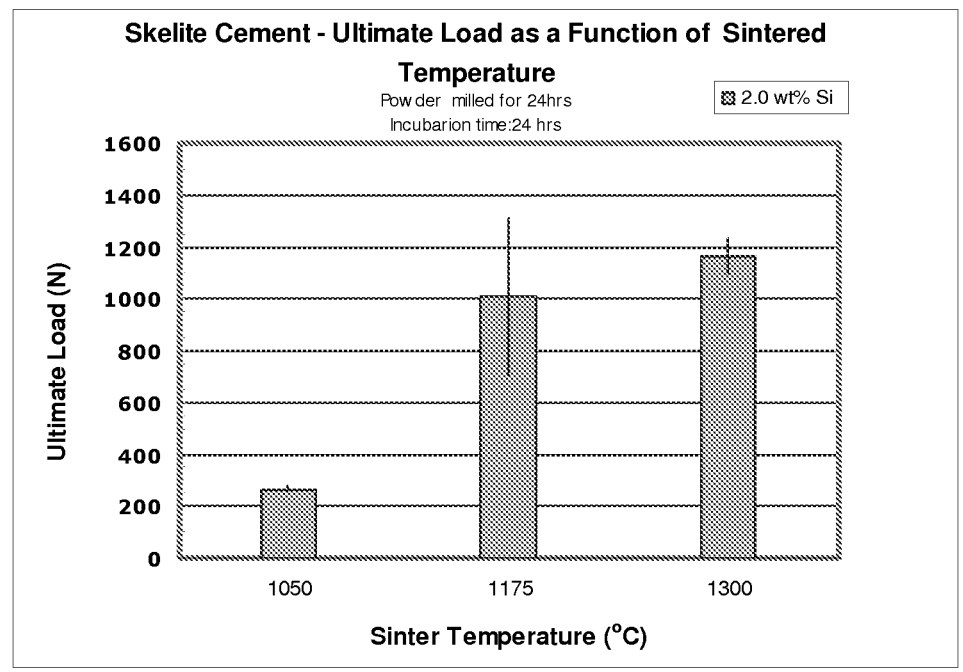
FIG. 4 illustrates the ultimate load as a function of sintering temperature of the cement precursor when utilizing 2.0 wt % silicon addition during the cement precursor manufacturing process.

The use of different thermal profiles in the calcination/sintering of the precursor to the biomineral phase also influences mechanical performance, as noted in FIG. 4.

Example 3

Optimizing the Mechanical Performance of a Biphasic Calcium Phosphate Cement

An evaluation of the critical parameters influencing the properties of the cement in combination with the biopolymer network was undertaken to assess the effect of different ratios of mixture components on mechanical performance and the ability to attain an interconnected network.

A series of cements containing biopolymer particles was prepared and evaluated for ultimate load and architecture.

Figure 5:
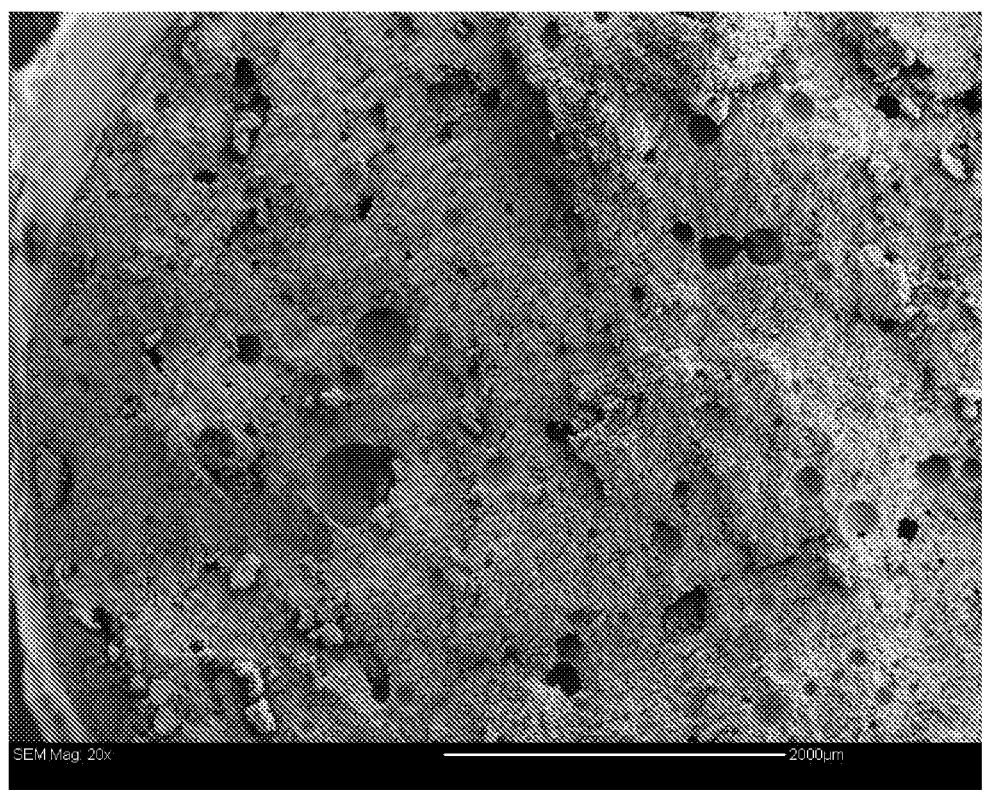
FIG. 5 shows a biphasic calcium phosphate cement of the invention with an incorporated biopolymer network enabling progressive therapeutic agent release and new tissue integration.

FIG. 5 is an SEM of a fracture face through the cement that illustrates the formation of a network of pores in the set cement after 24 hours of incubation in simulated biological fluids (SBF) at 37 C.

Figure 6:
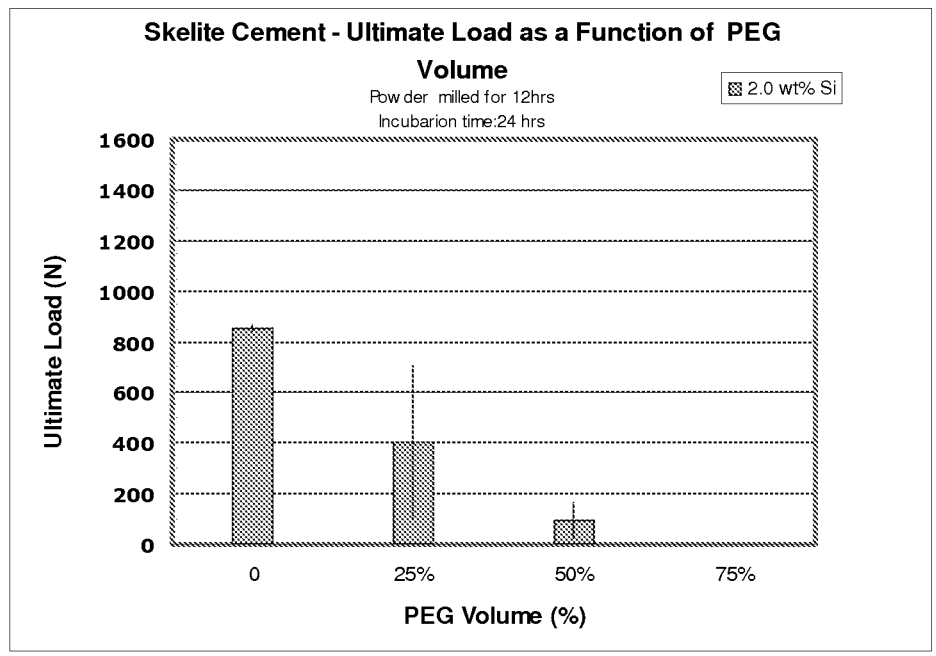
FIG. 6 illustrates the ultimate load as a function of volume % of PEG addition.

The influence of the biopolymer network on the ultimate load of the composition is highlighted in FIG. 6. As the level of the biopolymer increases, the cement is unable to form a rigid structure and the composition has minimal structural performance. While there is no specific strength requirement for the filling of bone voids that are not intrinsic to the structural stability of the skeleton, a measure of strength is advantageous in orthopedic applications where the implant ultimately incurs physiological loading.

Example 4

Incorporating Therapeutic Agents into the Cement 4 g of Skelite (silicon-substituted calcium phosphate particles), 1 g of PEG, 1.5 g of $Na_2HPO_4$ were blended together as a powder mixture, which was then combined with 1.5 ml of a rhBMP-2 solution from an Infuse Kit where each milliliter of the rhBMP-2 solution contains:
1.5 mg of rhBMP-2;
5.0 mg sucrose;
25 mg glycine;
3.7 mg L-glutamic acid;
0.1 mg sodium chloride;
0.1 mg polysorbate 80; and
1.0 mL of sterile water.

Cement samples with the above formulation and preparation were evaluated for their ability to encourage bone generation in a rabbit lumbar intertransverse process fusion model. In the surgical procedure, the transverse processes (TP) are dissected. The L5 and L6 TPs are then decorticated with a high-speed burr. Following mixing of the cement at the time of surgery, approximately 3.0 cc of graft material per side is implanted between the TPs. The animals are evaluated 8 weeks post surgery to assess the presence of fully-bridging lumbar intertransverse process spine fusions.

Example 5

Accelerant Concentration

In order to compare alternate formulations, a ranking system was devised wherein five concentrations of accelerant were utilized and rated against the following scale (note that all ranking assessments were subjective):

| Ranking | Description |
| --- | --- |
| 0 | Putty handling, wherein the putting is sticky to the touch. |
| 1 | Non-slumping & adhesive, wherein a cube can be formed, but wherein the cube remains slightly sticky to the touch. |
| 2 | Non-slumping & non-adhesive, wherein the cube is no longer sticky to the touch, but can still be deformed easily when pressure is applied. |
| 3 | Stiff yet still slightly deformable. |
| 4 | Substantially "set," but yet not rigid (the cube is resistant to distortion). |

The hydration levels (and corresponding $Na_2HPO_4$ quantity) were adjusted to result in a consistent 'Putty' like characteristic following initial mixing. A series of $Na_2HPO_4$ solutions were prepared using Milli-Q water and then added to the combination of silicon substituted calcium phosphate and PEG. The powder mixture (4 g of powdered (Milled 12 hrs) silicon substituted calcium phosphate and 1 g PEG 20000 with a particle size of about 150-212 microns) and the liquid were mixed for about 1.5 minutes and then ranked at various times according to the scale above.

| Sample | $Na_2HPO_4$ Buffer Conc. | $Na_2HPO_4$ Quantity (g) | Milli-Q (mL) | Rank at 20 min. | Rank at 30 min. | Rank at 40 min. |
| --- | --- | --- | --- | --- | --- | --- |
| 1 | 2.5% | 0.035 | 1.4 | 1 | 1 | 2 |
| 2 | 5% | 0.075 | 1.5 | 2 | 3 | 3 |
| 3 | 10% | 0.160 | 1.6 | 2 | 3 | 4 |
| 5 | 20% | 0.340 | 1.7 | 2 | 3 | 4 |

Note that at the 20% buffer concentration (Sample 5), the level of $Na_2HPO_4$ exceeds the solubility point.

Example 6

Accelerant in the Powder

The setting time for the cement when the $Na_2HPO_4$ was added in dry form to the powder and the combined powder added to the water. The powder mixture and liquid were mixed for about 1.5 minutes and then ranked at various times according to the scale above. The calcium phosphate and PEG ratio was also the same as Example 5.

| Sample | Implied $Na_2HPO_4$ Conc. | $Na_2HPO_4$ Quantity (g) | Milli-Q (mL) | Rank at 20 min. | Rank at 30 min. | Rank at 40 min. |
| --- | --- | --- | --- | --- | --- | --- |
| 1 | 2.5% | 0.035 | 1.4 | 1 | 1 | 3 |
| 2 | 5% | 0.075 | 1.5 | 1 | 2 | 3 |
| 3 | 10% | 0.160 | 1.6 | 1 | 3 | 4 |
| 4 | 15% | 0.225 | 1.7 | 3 | 4 | 4 |
| 5 | 20% | 0.340 | 1.7 | 3 | 4 | 4 |

Note that at the 20% buffer concentration (Sample 5), the level of $Na_2HPO_4$ exceeds the solubility point.

Example 7

Accelerant in the Powder in Combination with a Therapeutic Agent

The setting time for the cement formulations when admixed with BMP-2 in the buffer supplied with INFUSE®, with the $Na_2HPO_4$ supplied in the powder. BMP-2 from an InFuse® kit was rehydrated in the buffer supplied and then combined with the silicon substituted calcium phosphate, polyethyleneglycol (PEG) and sodium phosphate powder to make a cement (4 g of silicon substituted calcium phosphate, 1 g PEG 20000 with a particle size of about 150-212 microns, and $Na_2HPO_4$ as indicated).

| Sample | Implied $Na_2HPO_4$ Conc. | $Na_2HPO_4$ Quantity (g) | Buffer (mL) with BMP | Rank at 20 min. | Rank at 30 min. | Rank at 40 min. |
| --- | --- | --- | --- | --- | --- | --- |
| 1 | 2.5% | 0.035 | 1.4 | 2 | 3 | 3 |
| 2 | 5% | 0.070 | 1.4 | 2 | 3 | 4 |
| 3 | 10% | 0.150 | 1.5 | 3 | 4 | 4 |
| 4 | 15% | 0.240 | 1.6 | 3 | 4 | 4 |
| 5 | 20% | 0.360 | 1.8 | 4 | 4 | 4 |

Note that at the 20% buffer concentration (Sample 5), the level of $Na_2HPO_4$ exceeds the solubility point. An InFuse ® kit provides a solution having 1.5 mg/ml of rhBMP-2, 5 mg/ml sucrose, 25 mg/ml glycine, 3.7 mg/ml L-glutamic acid, 0.1 mg/ml polysorbate and 0.1 mg/ml NaCl.

Example 8

Compression Strength

The mechanical compression strength for the silicon substituted calcium phosphate cement was analyzed. Six samples were prepared as described herein, either by combining water with a powder mixture of silicon substituted calcium phosphate, sodium phosphate ($Na_2HPO_4$), and PEG or by combining a silicon substituted calcium phosphate and PEG powder mixture, with water containing sodium phosphate ($Na_2HPO_4$). The prepared mixtures were then loaded into cylindrical Teflon moulds (10 mm D.×12 mm H); the moulds were immersed in a simulated body fluid (SBF) solution (in this case, PBS) and kept in an incubator at 37° C. for 24 hrs. The samples were subsequently removed from the die and mechanically tested using a universal testing machine (MTS). The specimen to be tested was placed on the lower platen of the machine and a constant axial compression displacement was applied to the specimen at a rate of 0.1 mm/sec until reaching specimen failure, as indicated by a severe drop in the load-displacement curve.

Figure 7:
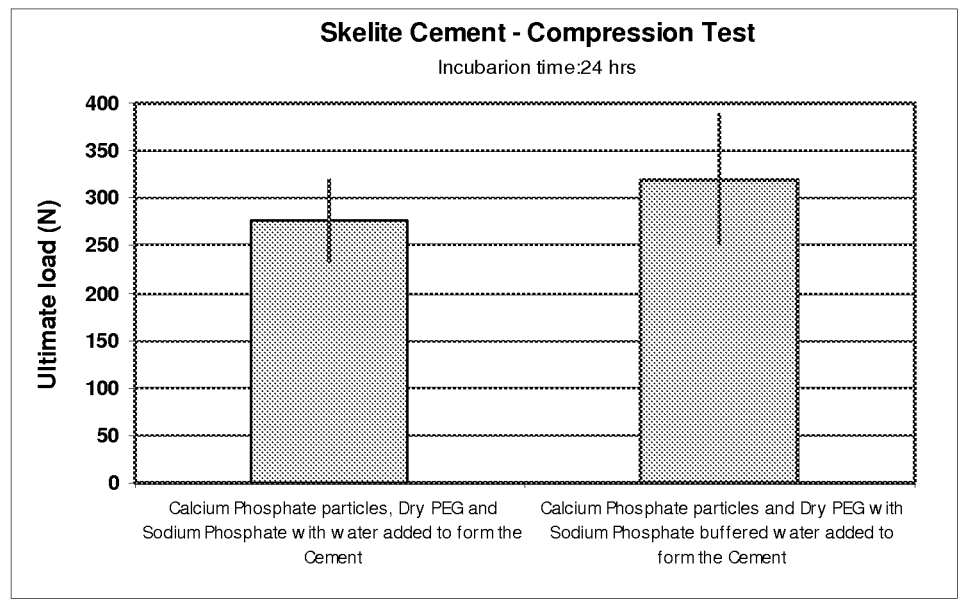
FIG. 7 illustrates that the ultimate load is not adversely affected by premixing the PEG, calcium phosphate particles and sodium phosphate.

The tests confirm that the powder components can be premixed without affecting performance (see FIG. 7)

| | Formulation | | | |
|---|---|---|---|---|
| | Pre-mixed powder + Water | Powder + Buffer Sol. | Pre-mixed powder + Water | Powder + Buffer Sol. |
| Consistency | Putty | Putty | Injectable | Injectable |
| Compression load (N) sample 1 | 248.2 | 430 | 299.5 | 166.5 |
| Compression load (N) sample 2 | 286.1 | 226.4 | 258.9 | 115.1 |
| Compression load (N) sample 3 | 309.2 | 313.3 | 357.6 | 240.2 |
| Compression load (N) sample 4 | 219.2 | 349.5 | 325.1 | 231.9 |
| Compression load (N) sample 5 | 334.8 | 320.2 | 337.6 | 181 |
| Compression load (N) sample 6 | 261.3 | 280 | 231.1 | 140.6 |
| Average | 276.5 | 316.6 | 301.6 | 179.2 |
| Standard Deviation | 42.1 | 68.4 | 48.5 | 49.5 |

Example 9

Accelerant in the Powder

The setting time for the cement is measured when $Na_2HPO_4$ and $CaCl_2$ are added in dry form to the powder and the combined powder is then added to the water. The powder mixture and liquid are mixed for about 1.5 minutes and then ranked at various times according to the scale above. Setting times are found to increase relative to those found in Examples 5 and/or 6, however, the dissolution rate of a therapeutic agent is found to decrease.

Although preferred embodiments of the present invention are described in detail herein, it will be understood by those skilled in the art that variations may be made thereto without departing from the spirit of the invention.

Each of the published articles, patents and patent applications identified in this specification are hereby incorporated by reference in their entirety into the specification.

What is claim is:

1. A settable biphasic composition in the form of a flowable paste, comprising: a plurality of individual calcium phosphate particles wherein the calcium phosphate particles have a portion of the phosphate substituted with silicon; a liquid capable of supporting calcium phosphate precipitation; a bioabsorbable polymer at a concentration that enable tissue ingrowth into the composition upon polymer absorption; and sodium phosphate or potassium phosphate.

2. The settable biphasic composition of claim 1, wherein the composition is a bone cement.

3. The settable biphasic composition of claim 2, wherein the calcium phosphate particles are at least 65% tricalcium phosphate.

4. The settable biphasic composition of claim 1, wherein the bioabsorbable polymer comprises polyethylene glycol or dextran.

5. The settable biphasic composition of claim 4, further comprising one or more therapeutic agents.

6. The settable biphasic composition of claim 5, wherein the therapeutic agent is selected from the group consisting of BMP-2, BMP-7, TGFβ, GDF-5, and combinations thereof.

7. The settable biphasic composition of claim 5, wherein the therapeutic agent comprises an analgesic or an antimicrobial agent.

8. The settable biphasic composition of claim 1, wherein the bioabsorbable polymer is present at less than 75% by weight of the bioabsorbable polymer and calcium phosphate particles mixture.

9. The settable biphasic composition of claim 1, further comprising potassium phosphate, wherein the bioabsorbable polymer comprises dextran.

10. A method for the production of a calcium phosphate composition, the method comprising: mixing a silicon-substituted calcium phosphate powder, a biodegradable polymer, and a setting accelerant with a therapeutic agent and an aqueous solution; and producing a flowable silicon-substituted calcium phosphate paste having a therapeutic agent distributed therein.

11. The method according to claim 10, wherein biodegradable polymer comprises polyethylene glycol (PEG).

12. The method according to claim 10, wherein the setting accelerant comprises sodium phosphate or potassium phosphate at a concentration of between about 0.5% and about 15% by weight.

13. The method according to claim 10, wherein the silicon-substituted calcium phosphate powder is prepared by a process comprising sintering a silicon doped calcium phosphate powder at a temperature between about 1000° C. and about 1300° C.

14. The method according to claim 13, wherein the silicon-substituted calcium phosphate powder has up to about 5 weight percent silicon.

15. The method according to claim 14, wherein the silicon-substituted calcium phosphate powder has between about 0.5 and about 2.0 weight percent of silicon.

16. The method according to claim 14, wherein the biodegradable polymer is present at less than 30% by weight of the calcium phosphate composition.

17. The method according to claim 10, wherein the silicon-substituted calcium phosphate powder and biodegradable polymer are mixed together prior to addition of the aqueous solution.

18. A silicon-substituted calcium phosphate cement kit comprising: silicon-substituted calcium phosphate particles, a biocompatible polymer, and a setting accelerator in a first container; an aqueous solution in a second container; and a lyophilized therapeutic agent in a third container, wherein the silicon-substituted calcium phosphate particles, biocompatible polymer and aqueous solution are mixed to form a settable silicon-substituted calcium phosphate paste.

19. The silicon-substituted calcium phosphate cement kit of claim 18, wherein the therapeutic agent comprises BMP-2, BMP-7 or GDF-5.

20. The silicon-substituted calcium phosphate cement kit of claim 19, further comprising a calcium salt selected from the group consisting of calcium chloride, calcium citrate, calcium carbonate, calcium gluconate, calcium phosphate, calcium sulfate and combinations thereof.

* * * * *